United States Patent [19]

Listemann et al.

[11] Patent Number: 4,968,841

[45] Date of Patent: Nov. 6, 1990

[54] SYNTHESIS OF ETHYLIDENE BISFORMAMIDE FROM VINYL ACETATE

[75] Inventors: Mark L. Listemann, Whitehall; Ronald Pierantozzi, Orefield; Robert K. Pinschmidt, Jr., Allentown, all of Pa.

[73] Assignee: Air Products and Chemicals, Inc., Allentown, Pa.

[21] Appl. No.: 436,567

[22] Filed: Nov. 14, 1989

[51] Int. Cl.$^5$ ............................................. C07C 233/34
[52] U.S. Cl. ...................................... 564/159; 564/152
[58] Field of Search ........................................... 564/159

[56] References Cited

U.S. PATENT DOCUMENTS

| | | | |
|---|---|---|---|
| 4,018,826 | 4/1977 | Gless, Jr. et al. | 260/583 |
| 4,176,136 | 11/1979 | Brenzel | 564/159 |
| 4,322,271 | 3/1982 | Jensen et al. | 204/73 |
| 4,490,557 | 12/1984 | Dawson et al. | 564/159 |
| 4,567,380 | 1/1986 | Murao et al. | 564/215 |
| 4,578,515 | 3/1986 | Dawson et al. | 564/215 |
| 4,670,591 | 6/1987 | Oftring et al. | 564/224 |
| 4,906,777 | 3/1990 | Pinschmidt, Jr. et al. | 564/215 |

FOREIGN PATENT DOCUMENTS 3443463 4/1986 Fed. Rep. of Germany .

OTHER PUBLICATIONS

D. J. Dawson et al., "Poly(vinylamine Hydrochloride) Synthesis and Utilization for the Preparation of Water-Soluble Polymeric Dyes," Journal of the American Chemical Society, 98, pp. 5996–6000 (1976).

Journal of Organic Chemistry, vol. 36, No. 2, p. 351 (1971).

R. H. Summerville, et al., "Synthesis of N-Vinyl Acetamide and Preparation of Some Polymers and Copolymers," ACS, Polymer Reprints, (1983) 24, pp. 12–13.

S. Takese, et al., "The Reaction of Vinyl Acetate with Fatty Amide", Institute of Chemistry, Coll. of Gen. Education, Osaka Univ., pp. 7–9.

E. Bayer, et al., "Homogeneous Catalytic Vinylation of Cyclic Imides and Lactams for the Synthesis of N-Vinyl Monomers," Angew. Chem. Int. Ed. Engl., (1979) 18(7) pp. 533–534.

*Primary Examiner*—Richard L. Raymond
*Assistant Examiner*—Susan P. Treanor
*Attorney, Agent, or Firm*—Mark L. Rodgers; William F. Marsh; James C. Simmons

[57] ABSTRACT

Ethylidene bisformamide is produced in high selectivity by the reaction of formamide with vinyl acetate in a molar ratio of at least 1:1 at a temperature from about 60° to 150° C. in the presence of a catalyst comprising an acid salt of mercury of which the parent acid has a pKa less than about 3.8.

11 Claims, No Drawings

SYNTHESIS OF ETHYLIDENE BISFORMAMIDE FROM VINYL ACETATE

TECHNICAL FIELD

The present invention relates to a process for making ethylidene bisformamide.

BACKGROUND OF THE INVENTION

Poly(vinylamines) are polymers which can be prepared over a broad range of molecular weights. Depending upon their average molecular weight, such polymers find various uses in the preparation of dyes, pharmaceuticals, flocculation agents and as viscosifiers in papermaking and enhanced recovery vinylamines are too unstable to be polymerized, these polymers are prepared by hydrolysis of poly(N-vinylamides) such as poly(N-vinylacetamide). The monomer for this polymer is made by the reaction of acetamide and acetaldehyde to form ethylidene bis-acetamide which is then pyrolyzed to the N-vinylacetamide. This reaction is described in Dawson, et. al. JACS, 98, pg. 5996–6000 (1976). An improvement in the in Dawson, et. al. basic process is described as a reaction between acetamide and acetaldehyde over a sulfuric acid catalyst, rather than perchloric acid, in order to form ethylidene bis-acetamide which was then pyrolyzed to form N-vinylacetamide. The N-vinylacetamide was polymerized and the polymer subjected to hydrolysis to form poly(vinylamine hydrochloride) which was used in preparing polymeric azo dyes.

U.S. Pat. No. 018,826 (1977) also discloses a method of making poly(vinylamine) by hydrolyzing poly(N-vinylacetamide) which has been formed by thermally cracking ethylidene bis-acetamide prepared by reacting acetaldehyde and acetamide using an aqueous mineral acid catalyst.

It was known that a similar reaction could take place between formamide and acetaldehyde in an aqueous solution of hydrochloric acid as described in "Journal of Organic Chemistry". Volume 36, No. 2, pg. 351 (1971}, which describes a method for making 1.1-bis(-formamido) ethane, another name for ethylidene bisformamide.

U.S. Pat. No. 4,490,557 (1984) discloses the preparation of ethylidene bisformamide from acetaldehyde and formamide using an acidic catalyst and an ammonia scavenger, such as acetic anhydride. Wiped film evaporation is used to recover the ethylidene bis-formamide which can be cracked to form N-vinylformamide, a monomer useful in preparing poly(N-vinylformamide) which can then be hydrolyzed to poly(vinylamines). useful in making dyes and pharmaceuticals. The acidic catalysts which are disclosed include acidic ion exchange resins, of which several examples are given including the preferred operating example. Alternatively, mineral acids, such as sulfuric or hydrochloric acid, or lower alkanoic acids, such as formic or acetic acids, can be used when added in catalytically effective amounts. Such amounts are stated to cover a broad range from about 0.001 to 1 mole of acid catalyst per mole of formamide.

Because of the difficulty in recovering polymerization grade monomers by the above described routes, others have sought to prepare N-vinylcarboxylic acid amides by different routes. U.S. 4,322,271 (1982) discloses that N-vinyl-N-alkyl-carboxylic acid amides can be obtained by removing an alcohol from N-α-alkoxyethyl-N-alkyl-carboxylic acid amides which have been made by prior alkylation and alkoxylation steps from N-ethyl-carboxylic acid amides.

Sommerville, et. al., ACS, Polymer Preprints. (1983) 24, 12–13, discloses preparing N-vinylacetamide from acetamide and the acetaldehyde dimethyl acetal. This process requires large excesses of the acetal, for example mole ratios of about 20 moles of acetal per mole of acetamide, in order to achieve practical yields and purities and is reported to fail in the corresponding reaction with formamide. U.S. Pat. No. 4,567,300 (1986) discloses, on the other hand, reacting formamide with acetaldehyde over a basic catalyst to form N-(α-hydroxyethyl) formamide instead of ethylidene bis-formamide. This process is unattractive because it requires two discrete steps, plus the handling of a solid intermediate and the disposal of salts.

U.S. 4,670.591 (1987}describes the synthesis of N-alkoxyethyl formamide from a vinyl ether and formamide. While this process is said to be effective with either an acidic or basic catalyst, the vinyl ethers are very expensive starting materials.

German Patent DE3443463 (1986) describes making N-vinylformamide using 1-cyanoethyl formamide. This process has the disadvantage of generating hydrogen cyanide which is toxic.

The above processes as routes to the manufacture of poly(vinylamines}all have disadvantages including difficult catalyst removal, toxic byproduct formation, low conversions or catalyst deactivation. A commercial process which does not have these disadvantages has yet to be developed. Ethylidene bis-formamide is still an attractive intermediate for the synthesis of N-vinylformamide as this product is stable and can be efficiently cracked thermally to form a 1:1 mixture of N-vinylformamide and formamide. Such a mixture can be purified by distillation as described in U.S. Pat. No. 4,578,515.

The preparation of ethylidene bis-formamide using strong acid catalysts as disclosed in U.S. 4.490.557. has the disadvantage that the strong acid catalyst residues must be removed from the ethylidene bis-formamide product prior to purification and cracking. Otherwise unwanted side reactions and loss of N-vinylformamide due to acid catalyzed degradation in the cracking step are observed. The use of the solid polymer acid resins, on the other hand, allows the removal of salts and catalyst as a solid from the liquid product. Unfortunately, however, in the synthesis of ethylidene bis-formamide the catalyst activity declines rapidly during the reaction, giving poor conversions. This is caused by the hydrolysis of formamide and neutralization of the catalyst with ammonia. Since water is produced in the synthesis of ethylidene bis-formamide and high levels of formamide are required to drive the synthesis reaction, it is not feasible to suppress the formation of ammonia using prior art technology. The result is poor conversions and impure product, probably arising from unwanted acetaldehyde self-condensation reactions. It is highly desirable, therefore, to find a way of improving the yields of ethylidene bis-formamide in such reactions and reducing the loss of formamide by hydrolysis.

Takase, et al., in a paper submitted to the Institute of Chemistry, College of General Education. Osaka University (Received October 11, 1967) describes the reaction of a fatty amide and vinyl acetate to produce ethylidene-bis-amide, using stannic salt as a catalyst in the presence of a large excess of vinyl acetate.

Bayer, et al. Angew. Chem. Int. Ed. Engl. (1979) 18(7), 533-534 disclose a reaction for the synthesis of N-vinyl imides using a large excess of vinyl acetate, i.e., about 27:1 over a sodium tetrachloropalladate catalyst.

BRIEF SUMMARY OF THE INVENTION

The present invention is a process for the synthesis of ethylidene bisformamide comprising reacting formamide with vinyl acetate in a formamide to vinyl acetate molar ratio of at least 1:1. The reaction is carried out at a temperature from about 60° to 150°C., in the presence of a catalyst comprising an acid salt of mercury chosen such that the parent acid has a pKa less than about 3.8. By employing an acidic catalyst comprising an acid salt of mercury and using a reactant formamide to vinyl acetate ratio of 1:1 or greater, high vinyl acetate conversions and high selectivity toward ethylidene bisformamide are achieved at high temperatures., i.e. about 60° to 150°C. The present process is advantageous in that high conversions and selectivities are realized at temperatures which allow for short reaction times.

DETAILED DESCRIPTION OF THE INVENTION

Ethylidene bisformamide is synthesized from vinyl acetate and formamide in the presence of a catalyst comprising an acid salt of mercury at a temperature from about 60°C. to 150°C. The reaction is carried out by mixing the reactants, typically in a stirred tank reactor, in a formamide to vinyl acetate molar ratio of at least 1:1. Suitable catalysts include strong acid salts of mercury, such as $Hg(O_2CCF_3)_2$, $Hg(O_3SCH_3)_2$, $Hg(O_3SCF_3)_2$ and mixtures thereof, and weak acid salts of mercury with strong proton acid cocatalysts, such as $Hg(OAc)_2$ with $H_2SO_4$ $CH_3SO_3H$ or a strong ion exchange resin such as Amberlyst 15 made by Rohm and Haas, Inc. The catalyst should be chosen such that the parent acid of the catalyst has a pKa less than about 3.8, since weaker acids, even at preferred reactant molar ratios are ineffective.

The reaction can be carried out at a wide range of pressures, including atmospheric or autogenous pressure and at temperatures ranging from 60°-150°C. with a range from about 60°-80°C. being preferred. The catalyst should be present in a concentration of from about 0.01 to 10 mole% based upon vinyl acetate, with about 2 mole% being preferred. The reactants should be present in a formamide to vinyl acetate ratio of at least 1:1, and preferably from about 2:1 to 3:1. By carrying out the reaction using these molar ratios and the above catalysts, high selectivity toward BIS product with high vinyl acetate conversion is obtained at temperatures (60°-150°C.) which afford greater reaction rates thereby reducing the required reaction time. Reaction times from about 1-8 hrs. are typical, with times from 3-5 hrs. being preferred.

Preferably the catalysts should be contacted with formamide, but not heated, before the introduction of vinyl acetate. Small amounts of solvent., e.g., 1:1 mole ratio solvent to vinyl acetate, such as acetonitrile or other formamide miscible moderately polar solvents may be used but are not required. Amide solvents should be avoided.

EXPERIMENTAL

The experimental procedures used to carry out the Examples below is as follows:

To a 25 ml 3 neck round bottom flask was charged successively mercuric acetate (0.236g. 0.74 mmol), formamide (4.999g. 111 mmol), and vinyl acetate (3.186g, 37 mmol). The flask was equipped with a reflux condenser/inert gas inlet, mechanical stirrer, and septum stopper. The flask was connected to a source of dry argon and a slow purge established. Once stirring started methanesulfonic acid (0.178g, 1.85 mmol) was added via syringe and the reaction heated to 60°C. The reaction products were analyzed using $^{13}C$ NMR.

The following examples were carried out to illustrate the present invention and are not meant to be limiting.

EXAMPLE 1

Runs were carried out using the above procedure to determine the effect of temperature on vinyl acetate conversion and Bis production for the reaction of vinyl acetate with formamide. The results are reported in Table 1 below.

TABLE 1

$$CH_2 = CHOAc + 3\ H_2NCHO \xrightarrow{0.02\ Hg(OAc)_2/0.05\ CH_3SO_3H}$$

| Run | Time (hr) | Temp. (°C.) | Vinyl Acetate Conversion | % Yield Bis | Selectivity to Bis (vs. Vinyl Acetate) |
|---|---|---|---|---|---|
| 1 | 2 | 25 | 14 | 6 | 43 |
| 2 | 1 | 40 | 12 | 15 | 100 |
| 3 | 2 | 60 | 97 | 92 | 95 |

The results reported in Table 1 above indicate that vinyl acetate conversion and Bis yield increase at higher temperatures while maintaining good selectivities.

EXAMPLE 2

Runs were carried out to determine the effect of various mercuric catalysts on the reaction of vinyl acetate with formamide. The reaction was carried out in accordance with the experimental procedure set out above using a formamide to vinyl acetate molar ratio of 3:1. The results of these runs are reported in Table 2 below.

TABLE 2

$$CH_2 = CHOAc + 3\ H_2NCHO \longrightarrow$$

| Catalyst (Mole Eq.) | pKa | Time (hr) | Temp. (°C.) | Vinyl Acetate Conversion | % Yield Bis | Selectivity to Bis (vs. Vinyl Acetate) |
|---|---|---|---|---|---|---|
| $Hg(OAc)_2$ (0.02) $CH_3SO_3H$ (0.05) | ~−3 | 2 | 60 | 97 | 92 | 95 |
| $Hg(O_2CCF_3)_2$ (0.02) | 0.23 | 2 | 80 | 81 | 74 | 91 |
| $Hg(OAc)_2$ (0.02) HCOOH (0.10) | 3.75 | 2 | 60 | 13 | 3 | 23 |

TABLE 2-continued

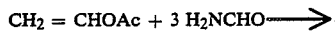
$CH_2 = CHOAc + 3\ H_2NCHO \longrightarrow$

| Catalyst (Mole Eq.) | pKa | Time (hr) | Temp. (°C.) | Vinyl Acetate Conversion | % Yield Bis | Selectivity to Bis (vs. Vinyl) Acetate) |
|---|---|---|---|---|---|---|
| Hg(OAc)$_2$ (0.02) | 4.75 | 4 | 80 | 4 | 0 | 0 |

The results reported in Table 2 above show that mercuric acetate/strong acid combinations as well as pure mercuric salts of strong acids (first two entries) are active and selective. A weaker acid cocatalyst (e.g., HCOOH, pKa 3.75) lowers activity substantially while mercuric acetate alone (pKa 4.75) is completely inactive.

EXAMPLE 3

Runs were carried out to determine the effect of both reactant ratio and temperature on product selectivity for the reaction of vinyl acetate with formamide over a Hg(OAc)$_2$/CH$_3$SO$_3$H catalyst. The results of these runs are reported in Table 3 following.

TABLE 3

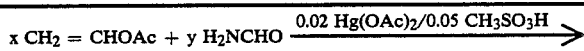
$x\ CH_2 = CHOAc + y\ H_2NCHO \xrightarrow{0.02\ Hg(OAc)_2/0.05\ CH_3SO_3H}$

| x VAM | y H$_2$NCHO | Temp (°C.) | Time (hrs) | % Yields[a] VAM | Acetic | Bis | H$_2$NCHO | VAM Conv. | Bis[b] Sel. | Acetate[c] M.B. | H$_2$NCHO[d] M.B. |
|---|---|---|---|---|---|---|---|---|---|---|---|
| 2.5 | 1 | 25 | 14 | 226 | 28 | 22 | 52 | 24 | 92 | 254 | 96 |
| 2.5 | 1 | 50 | 3 | 212 | 43 | 36 | 34 | 38 | 95 | 255 | 106 |
| 2.5 | 1 | 60 | 3 | 175 | 50 | 17 | 13 | 75 | 23 | 225 | 47 |
| 1 | 1 | 25 | 14 | 66 | 29 | 22 | 56 | 34 | 65 | 95 | 100 |
| 1 | 1 | 60 | 3 | 16 | 56 | 32 | 17 | 84 | 38 | 72 | 81 |
| 1 | 2 | 25 | 14 | 81 | 18 | 13 | 175 | 19 | 68 | 99 | 201 |
| 1 | 2[e] | 50 | 3 | 72 | 20 | 15 | 161 | 28 | 54 | 92 | 191 |
| 1 | 2[e] | 60 | 4 | 36 | 64 | 57 | 95 | 64 | 89 | 100 | 209 |
| 1 | 3 | 25 | 14 | 84 | 22 | 12 | 279 | 16 | 75 | 106 | 303 |
| 1 | 3 | 60 | 4 | 0 | 95 | 84 | 134 | 100 | 84 | 95 | 302 |
| 1 | 3 | 80 | 3 | 0 | 99 | 89 | 119 | 100 | 89 | 99 | 297 |

[a]% yields based on limiting reagent - formamide in the first three entries and vinyl acetate in the remainder.
[b]Bis selectivity = % yield Bis/vinyl acetate conversion × 100
[c]Acetate mass balace = % yields (vinyl acetate + acetic acid). Theoretical values are 250 for the first three entries and 100 for the remainder.
[d]Formamide mass balance = % yields (formamide + 2x Bis). Theoretical values are 100 for the first five entries, 200 for the next three, and 300 for the last three.
[e]One equivalent of CH$_3$CN added to prevent Bis precipitation.

The results reported in Table 3 above show that, when using the prior art stoichiometry as taught by Takase, et al., (2.5:1 vinyl acetate to formamide), at 25°C. one-half of the formamide was converted cleanly to Bis in 14 hours, but a 10fold excess of vinyl acetate to Bis remained. The selectivity to Bis remained high, at 50°C., but dropped substantially at 60°C. Lowering the vinyl acetate to formamide ratio from 2.5:1 to 1:1 lowered the selectivity at 25°c. substantially (92 vs. 65%) but increased the selectivity at 60°C. (23 vs. 38%). A 1:2 vinyl acetate to formamide ratio afforded moderate selectivities (68 and 54%) at 25 and 50°C. and an 89% selectivity at 60°C. A 1:3 vinyl acetate to formamide ratio afforded good (75%) selectivity at 25°C, but conversion was only 16%. At 60-80°C. vinyl acetate was completely consumed and the selectivities increased to 84-89%.

The distinguishing feature of this process is the relationship between reactant ratio and temperature. Reactions with vinyl acetate to formamide ratios of greater than 1:1 require low temperatures to maintain high selectivity, and consequently suffer from modest rates and excessive vinyl acetate recycle. In contrast, reactions with vinyl acetate to formamide ratios of 1:1 or less operate more selectively at higher temperatures, which affords greater rates and minimizes reactant recycle. The 1:1 stoichiometry, although not preferred, illustrates the transition between these two regimes. At 1:1, the reaction was still more selective at low temperature, but the loss in selectivity when the temperature was increased was less severe than that observed for 2.5:1. Thus, it is possible to synthesize Bis in high conversion and selectivity with modest (3-4 hour) reaction times at this ratio. Accordingly, the preferred vinyl acetate to formamide ratio is typically 1:2-3.

Having thus described the present invention, what is now deemed appropriate for Letters Patent is set out in the following appended claims.

What is claimed is:

1. A process for the synthesis of ethylidene bisformamide comprising reacting formamide with vinyl acetate, in a formamide to vinyl acetate molar ratio of at least 1:1, at a temperature from about 60° to 150°C., in the presence of a catalyst comprising an acid salt of mercury of which the parent acid has a pKa less than about 3.8.

2. A process in accordance with claim 1 which is carried out at atmospheric pressure.

3. A process in accordance with claim 1 which is carried out at autogenous pressure.

4. A process in accordance with claim 1 wherein said catalyst is present in an amount from 0.01 to 10 mole% based upon vinyl acetate.

5. A process in accordance with claim 1 which is carried out at a temperature from 60° to 80°C.

6. A process in accordance with claim 1 wherein said formamide to vinyl acetate ratio is at least 2:1.

7. A process in accordance with claim 1 wherein said acid salt of mercury is selected from the group consisting of $Hg(O_2CCF_3)_2$, $Hg(O_3SCH_3)_2$, $Hg(O_3SCF_3)_2$ and mixtures thereof.

8. A process in accordance with claim 1 wherein said catalyst comprises $Hg(OAc)_2$ with a strong proton acid cocatalyst.

9. A process in accordance with claim 8 wherein said strong proton acid cocatalyst is $H_2SO_4$, $CH_3SO_3H$, or a strong ion exchange resin.

10. A process in accordance with claim 1 which is carried out in the presence of a formamide miscible moderately polar solvent.

11. A process in accordance with claim 10 wherein said solvent is acetonitrile.

* * * * *